United States Patent
Boese et al.

(10) Patent No.: US 7,315,605 B2
(45) Date of Patent: Jan. 1, 2008

(54) METHOD AND DEVICE FOR RECONSTRUCTING A 3D IMAGE DATA SET OF A MOVING OBJECT

(75) Inventors: Jan Boese, Eckental (DE); Günter Lauritsch, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/453,604

(22) Filed: Jun. 15, 2006

(65) Prior Publication Data

US 2006/0285632 A1 Dec. 21, 2006

(30) Foreign Application Priority Data

Jun. 16, 2005 (DE) ...................... 10 2005 027 963

(51) Int. Cl.
 *A61B 6/00* (2006.01)
(52) U.S. Cl. .......................... 378/8; 378/901; 382/275; 600/428
(58) Field of Classification Search ............. 378/4–27, 378/901; 382/130–132, 275; 600/425, 427, 600/428
See application file for complete search history.

(56) References Cited

U.S. PATENT DOCUMENTS

| 5,550,892 A | 8/1996 | Katsevich et al. | |
| 2006/0133564 A1* | 6/2006 | Langan et al. ................. | 378/8 |

FOREIGN PATENT DOCUMENTS

| WO | WO 97/49065 A1 | 12/1997 |
| WO | WO 01/85030 A1 | 11/2001 |

OTHER PUBLICATIONS

Jed D. Pack and Frédéric Noo, "Dynamic Computed Tomography with Known Motion Field", Medical Imaging, 2004, pp. 2097-2104, Proceedings of SPIE vol. 5370, SPIE, Bellingham, WA.
Christophe Blondel, Grégoire Malandain, Régis Vaillant, Nicholas Ayache, "4D Deformation Field of Coronary Arteries from Monoplane Rotational X-ray Angiography", International Congress Series 1256, 2003, pp. 1073-1078, Elsevier Science B.V.
Alexander. Katsevich, "Cone Beam Local Tomography", Society for Industrial and Applied Mathematics, 1999, pp. 2224-2246, vol. 59, No. 6.
Alfred K. Louis and Peter Maass, Contour Reconstruction in 3-D X-Ray CT, IEEE Transactions on Medical Imaging, Dec. 1993, pp. 764-769, vol. 12, No. 4.
Adel Faridani, Erik L. Ritman, Kennan T. Smith, "Local Tomography", Society for Industrial and Applied Mathematics, Apr. 1992, pp. 459-484, vol. 52, No. 2.

* cited by examiner

*Primary Examiner*—Courtney Thomas

(57) ABSTRACT

The invention relates to a method and device for reconstructing a 3D image data set of a moving object from a set of projection images, which were recorded at least partially one after the other from different projection directions. The projection images are hereby assigned by ECG gating to a motion phase of the object in each instance and an incomplete 3D image of the object is computed in this motion phase from these few projection images using local tomography. Motion fields are determined from these 3D images and are used during the final 3D image reconstruction for motion correction.

11 Claims, 5 Drawing Sheets

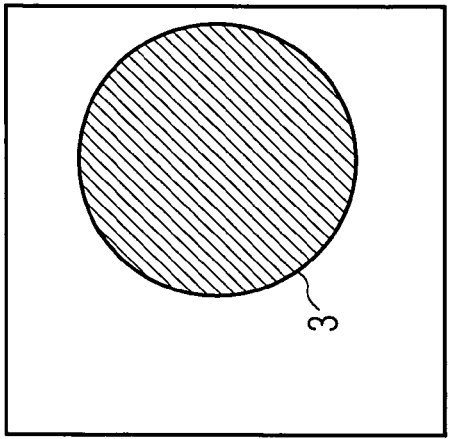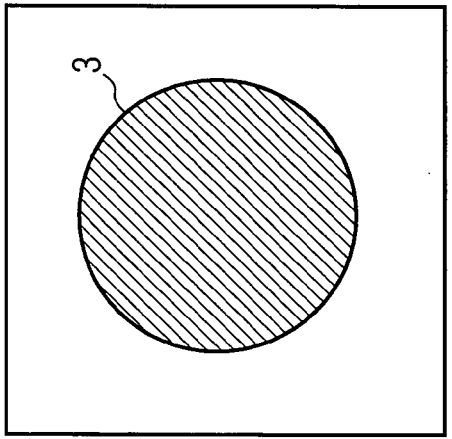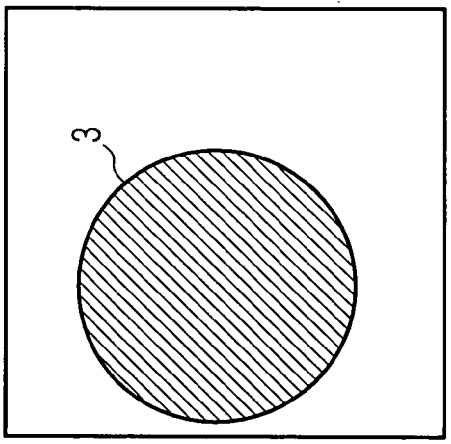
FIG 1
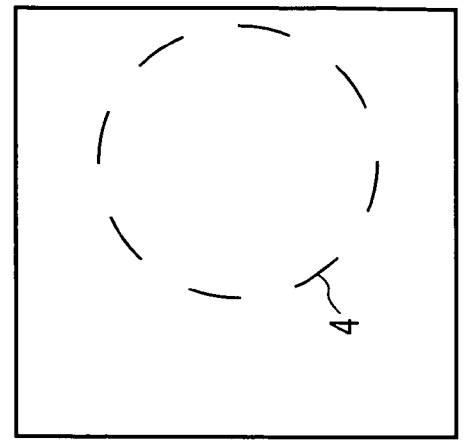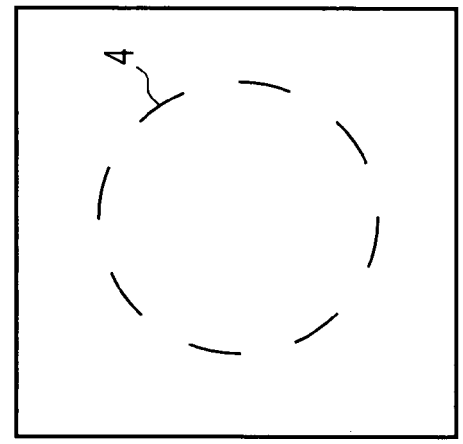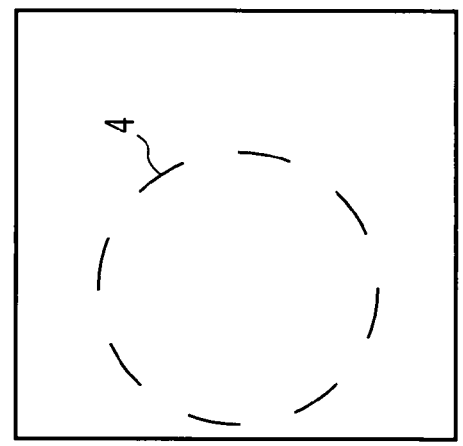
FIG 2

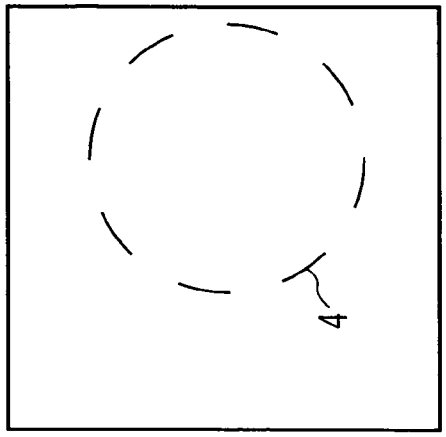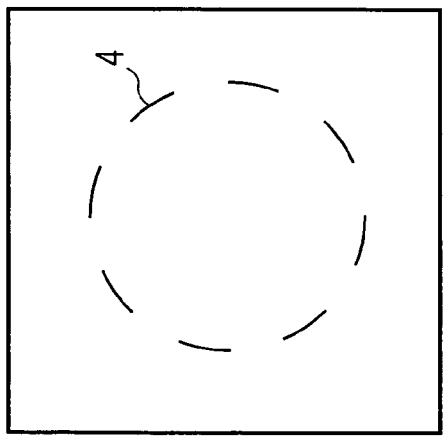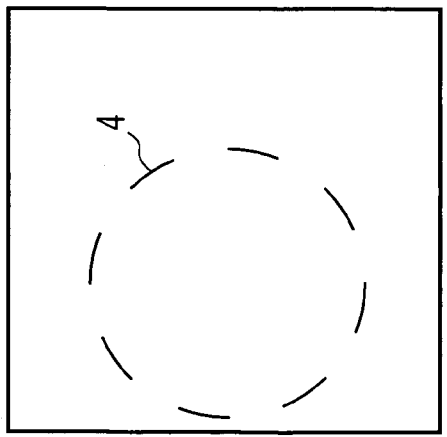
FIG 3
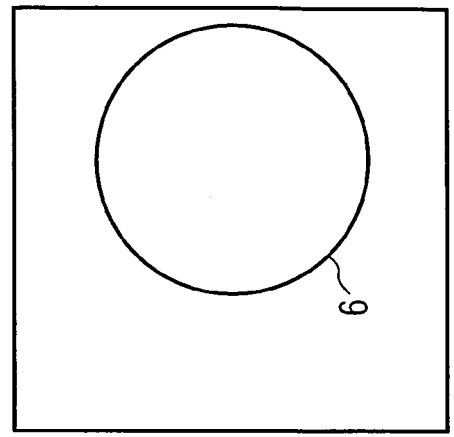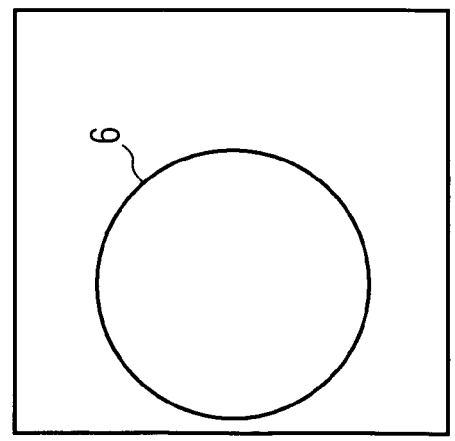
FIG 4

METHOD AND DEVICE FOR RECONSTRUCTING A 3D IMAGE DATA SET OF A MOVING OBJECT

CROSS REFERENCE TO RELATED APPLICATIONS

This application claims priority of German application No. 10 2005 027 963.5 filed Jun. 16, 2005, which is incorporated by reference herein in its entirety.

FIELD OF THE INVENTION

The invention relates to the field of 3D imaging and in particular a method and device for reconstructing a 3D image data set of a moving object from a set of projection images, which were recorded one after the other from different projection directions. The invention is used in particular in medical x-ray systems.

BACKGROUND OF THE INVENTION

Standard x-ray images are projection images, in which a three-dimensional (3D) object is x-rayed and projected onto a two-dimensional (2D) surface. Depth information is thereby lost. It is however possible to reconstruct a 3D image data set of the object from a large number of projection images, which were recorded from different projection directions over an angle range of at least 180°. If the required angle range has been scanned completely, these so-called tomographic 3D reconstruction methods require no previous knowledge of the object to be reconstructed.

Specialist computed tomographs (CTs) specifically for the purpose are generally used for 3D imaging using X-ray tomography. These devices have an annular system, comprising x-ray detectors and an x-ray tube, that rotates about the patient at high speed, thereby recording numerous projection images from any size of angle range.

For image-controlled diagnostic or surgical interventions, in which 2D projection images are recorded in an ongoing fashion during the intervention, what are known as interventional x-ray systems such as angiography systems or (mobile) x-ray C-arm systems are used. In the latter case the x-ray tube and x-ray detector are attached to opposing arms of a C-arm that can be moved freely about the patient, to allow x-ray images to be recorded from any projection direction.

Such systems can currently be used to generate 3D image data sets in the same manner as with computed tomographs. To this end the x-ray tube and detector are rotated over an angle range of typically approx. 200° during recording and 3D reconstructions are then calculated. When vessels are recorded, this method is referred to as 3D rotational angiography.

Because of the relatively long rotation times of typically 3 to 20 seconds compared with CT, such imaging is however restricted to non-moving organs and structures. In the case of the heart and coronary arteries, tomographic methods cannot be used with interventional x-ray devices, as the heart motion during recording causes the structures of the heart to appear smudged in the reconstructed 3D image data set.

There are different approaches to creating 3D reconstructions of the heart from recordings by interventional x-ray devices such as angiography systems despite such problems. With some methods for example the heartbeat is measured during image acquisition by recording an electrocardiogram (ECG). ECG gating is used so that only the projection images recorded during a relatively low-motion phase of the cardiac cycle are used for the reconstruction. What are known as "symbolic reconstruction methods" can be used to reconstruct specific, geometrically describable objects from these few projection images. Such objects are in particular blood vessels, which can be identified in the images by means of an intra-arterially injected high-contrast contrast agent. Such symbolic reconstruction methods, as disclosed for example in WO 97/49065 A1 and WO 01/85030 A1, have the disadvantage however that they make assumptions about the content of the image data set to be reconstructed and are also restricted to high-contrast objects. User interaction, e.g. the marking of specific landmarks in two or more images, is also essential.

Tomographic methods are also known, which use motion correction methods in order to be able to use more than just individual projection images for the reconstruction (see also C. Blondel, G. Malandain, R. Vaillant, N. Ayache: "4D deformation field of coronary arteries from monoplane rotational X-ray angiography", Computer Assisted Radiology and Surgery, 2003 Proceedings, Vol. 1256 of ICS, London, UK, June 2003, Elsevier Science B.V.). The basic idea is to use motion correction methods during image reconstruction. Blondel's method for example also uses symbolic reconstruction methods to create a model of the coronary arteries. This model is then tailored to the overall sequence of the projection images, which change during the cardiac cycle, in order to generate a four-dimensional "deformation field", showing the motion of the arteries during the course of the cardiac cycle. However this method also has the disadvantage of user interaction and is similarly restricted to high-contrast objects.

SUMMARY OF THE INVENTION

The object of the invention is therefore to provide a method and device for reconstructing a 3D image data set of a moving object from a set of projection images, requiring no user interaction but still supplying a high-quality image of the object.

The invention achieves this object with the features of the claims. Preferred embodiments of the invention are specified in the dependent claims.

The claimed method includes the following steps: (a) the set of projection images is divided into a number of subsets, each of which was recorded during a specific motion phase of the object; (b) local tomography is used to reconstruct an incomplete 3D image of the object from each subset of the projection images; (c) motion fields of the object are determined from the incomplete 3D images, each showing the motion of the object between two successive motion phases; and (d) the set of projection images is reconstructed to form a 3D image data set with motion correction being effected by means of the motion fields.

"Motion field" here refers to a vector field, which describes the displacement of the mapped object from the time of one imaging recording to the time of the next recording. The term displacement covers translation, rotation, deformation etc.

The invention uses methods from what is known as "local tomography" for the reconstruction of time-resolved motion fields of the moving object. In step (d) a standard 3D reconstruction of the data is effected taking into account the motion fields.

In a first step the set of projection images is divided into a number of subsets, each of which was recorded during a specific motion phase of the object. If the object is the heart or an organ of the body subject to the heartbeat, according to a preferred embodiment this is achieved by recording an electrocardiogram (ECG) and what is known as ECG gating. Only those projections originating from a specific time window of the cardiac cycle are selected from the full set of projections. An interval of around 5% to 30% of the cardiac cycle is typically selected such that the quantity of data or the number of projection images is reduced correspondingly. This incomplete subset of the projection images is now reconstructed using local tomography.

Local tomography methods are for example disclosed in the U.S. Pat. No. 5,550,892 and in the articles by A. Katsevich: "Cone Beam Local Tomography", SIAM J. Appl. Math., Vol. 59, No. 6, pp. 2224-2246, 1999, A. K. Louis, P. Maas: "Contour reconstruction in 3-D X-ray CT", IEEE Trans. Medical Imaging, Vol. 12, pp. 764-769, 1993 and A. Faridani, E. V. Ritman, K. T. Smith: "Local tomography", SIAM J. Appl. Math., Vol. 52, pp. 459-484 and pp. 1193-1198, 1992.

Local tomography methods are suitable for reconstructing a 3D image data set from incomplete two-dimensional parallel, cone or fan beam projection images. Incomplete here means that the projections may both originate from a restricted angle range (i.e. a smaller range than the 180°+ fan angle required for conventional 3D cone beam reconstruction, as is the case here) and may also be truncated.

The 3D image reconstructed therefrom using local tomography is however similarly incomplete, for example containing only certain segments of the mapped object. Local tomography is particularly suitable for reconstructing intensity changes (also known as edges or intensity edges) in the object, which often represent the contours of the object. To reconstruct a segment of an intensity edge with this method only projection data, the beams of which are essentially tangential or parallel to the edge segment, is required. According to a preferred embodiment therefore those segments of intensity edges, which are approximately tangential to the projection direction of an associated projection image, are reconstructed from a subset of the projection images originating from a limited angle range.

According to a further preferred embodiment these incomplete 3D images obtained by local tomography are processed before determination of the motion fields, by supplementing the sections between existing edge segments at least partially. To this end the existing intensity edges are first extracted and then the gaps between the existing segments are closed. This can be done by interpolation or any other suitable method, such as active contours, also known as "snakes". Snakes are parametric curves, which are tailored to image structures in an optimization step. Both image information and curve shape are taken into account here. Large parts of the contour of the moving object are preferably identifiable in the thus completed 3D images.

The edge gaps cannot however always be closed unambiguously. To avoid ambiguities in the assignment of the edge segments, the degree of change of an edge can be determined using special local tomography methods, as disclosed for example in U.S. Pat. No. 5,550,892, in order for example to be able to distinguish between the inside and outside of a surface.

After such completion of the contours, known image correlation or "curve matching" methods can preferably be used to map the edges of two successive images onto each other. The resulting assignment represents the motion field at the time between two images.

In the last step (d) the projection images are preferably subjected to a conventional 3D reconstruction method. The motion fields are however used here to effect motion correction. According to a preferred embodiment, the reconstruction volume is distorted before each projection is processed with the motion field corresponding to the respective motion phase. This method is known for motion field calculated in a different manner and is disclosed for example in the article by C. Blondel mentioned above.

The above-mentioned method is preferably used with an x-ray device with an x-ray tube and an x-ray detector, which rotate about a patient during recording, particularly preferably with an angiography system or a C-arm system.

The invention is also directed toward a device, which is preferably suitable for executing the method described above and is particularly preferably an x-ray angiography system or a C-arm system.

BRIEF DESCRIPTION OF THE DRAWINGS

Exemplary embodiments of the invention are described in more detail below with reference to the accompanying drawings, in which:

FIG. 1 shows a schematic diagram of three motion phases (frames) of a moving object;

FIG. 2 shows images of the object in FIG. 1 reconstructed using local tomography, each corresponding to one of the three motion phases;

FIG. 3 shows images of the object in FIG. 1 reconstructed using local tomography, each corresponding to one of the three motion phases;

FIG. 4 shows a schematic diagram of the images in FIGS. 2 and 3 supplemented by interpolation;

DETAILED DESCRIPTION OF THE INVENTION

For the purposes of illustration, FIG. 1 shows a circular object 3, which moves to and fro and thereby moves over three time steps (frames) from left to right. For the purpose of simplification the 2D reconstruction problem is considered in this example, with the circular focal trajectory in the plane of the paper. In other words the projection directions of the recorded (one-dimensional) projection images are in the plane of the paper.

Projection images are now taken of this object as it moves to and fro, by an imaging system rotating slowly about said object. During this time the motion status of said object is measured using any method. The projection images are divided into three subsets, each of which was recorded while the object was in the same motion phase (gating). This ECG gating step is marked with 30 in the flow diagram in FIG. 6. Each data subset covers only specific angle segments and is reconstructed to form an (incomplete) image using local tomography in step 32, said images being shown in FIG. 2. The edges (intensity changes) have already been extracted in FIG. 2 and it can be seen that only the edges parallel to the projection direction of the projection images associated with this subset were reconstructed. As 8 edge segments were reconstructed in each instance, the object clearly made 8 to and fro motions during one pass of the imaging system. This corresponds approximately to the number of heartbeats by the heart during an image recording lasting 8 seconds.

In the example shown only 3 motion phases were selected but during a clinical examination the cardiac cycle can also be divided into 6, 8, 10 or 12 time windows, which are preferably distributed at equal intervals over the cardiac cycle.

The images shown in FIGS. 2 and 3 are then further processed in a next step, by completing the edges reconstructed using local tomography. This step is optional and is therefore not shown in FIG. 6. Because of the simple geometric form of the object this is relatively simple in the example shown and can be achieved by means of known interpolation algorithms or by the "active contours" mentioned above. The images shown in FIG. 4 result, each showing the contours 6 of the object in the three time windows or motion phases.

Figure 5:
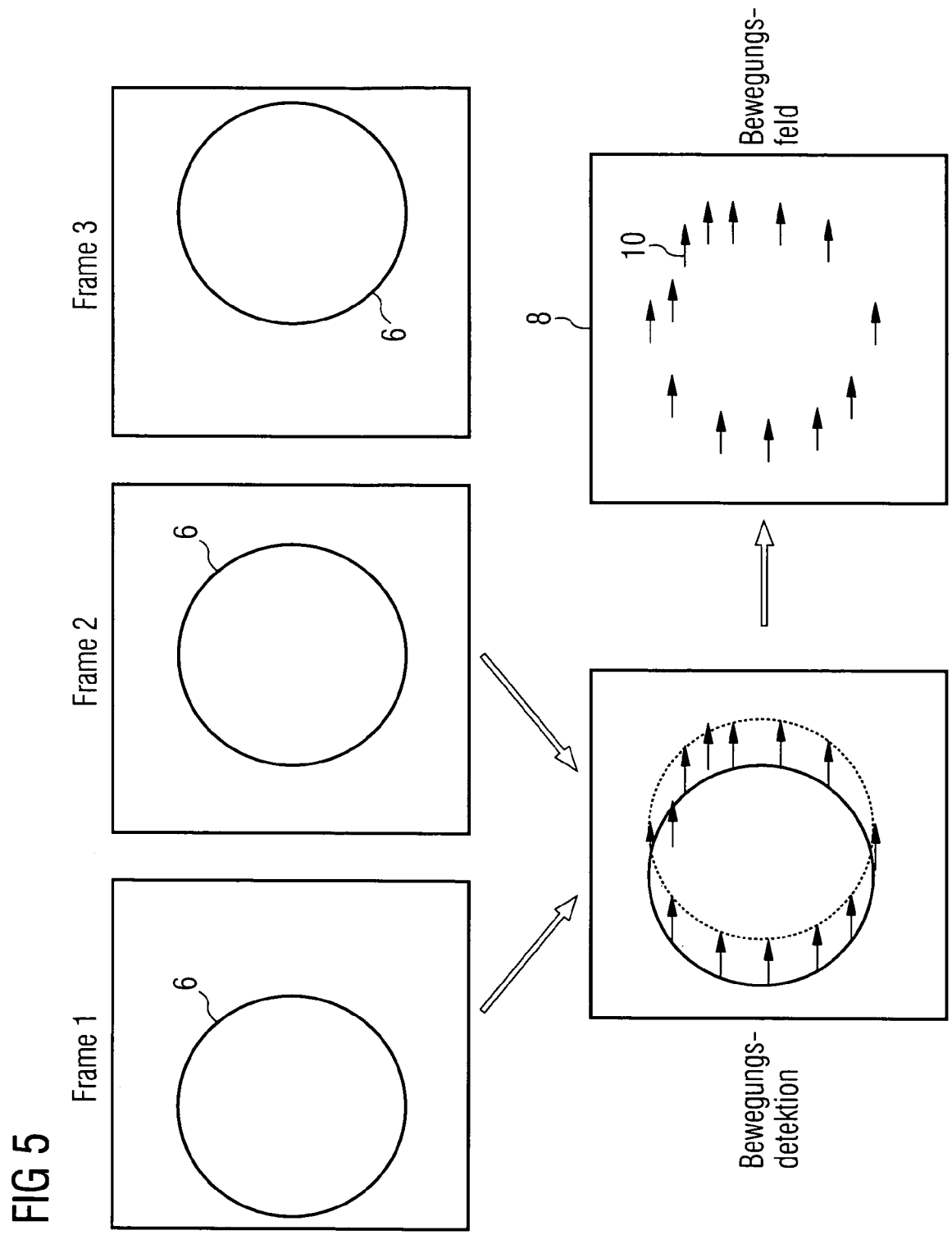
FIG. 5 shows a schematic diagram of the generation of the motion field from the images in FIG. 4.

After the contours have been completed, known image correlation or "curve matching" methods are used to map the edges of two successive images onto each other, as shown in FIG. 5. Two points representing the same point on the object are thereby mapped onto each other in each instance in two successive contour images 6 by means of a displacement vector 10 (step 34 in FIG. 6). The totality of the displacement vectors 10 gives the motion field 8 between two successive contour images 6. The motion field of the object 3 as a whole is determined by interpolation and extrapolation. In the literature "motion field" is often used to refer to the four-dimensional vector field, bringing together all the displacement vectors between all the successive contour images of a time series.

In the example shown the object 3 is rigid and all the displacement vectors 10 are therefore parallel to each other and of identical size but this would not be the case with the contracting motion of the heart.

Figure 6:
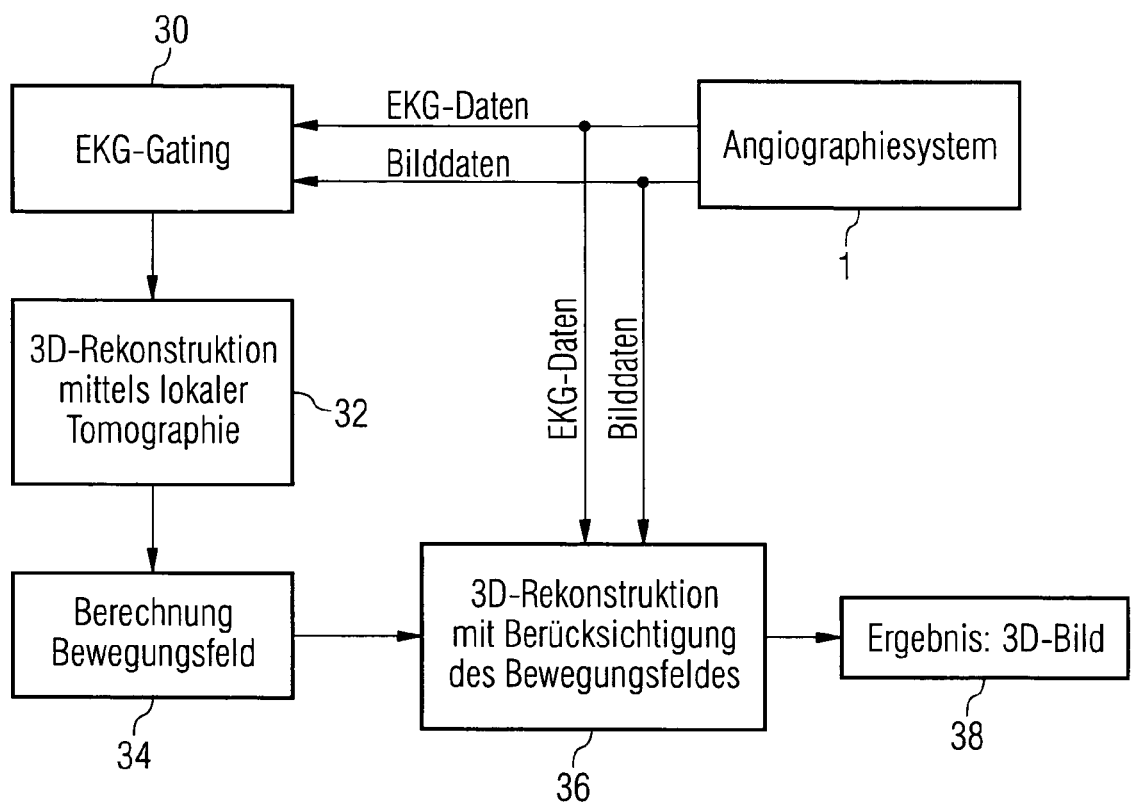
FIG. 6 shows a flow diagram, illustrating an exemplary embodiment of the claimed method.

The determined motion field 8 can now be used to produce a 3D reconstruction with motion correction such that a 3D image data set of the object 3 can be computed without or with significantly reduced motion artifacts (step 36 in FIG. 6). The 3D image grid is thereby distorted in each cardiac phase with the motion phase corresponding to the respective cardiac phase, as disclosed in the above-mentioned article by C. Blondel or in J. D. Pack, F. Noo: "Dynamic computed tomography with known motion field", Proc. SPIE, Vol. 5370, pp. 2097-2104, 2004.

The flow diagram in FIG. 6 shows an overview of the method steps 30 to 38 described above.

Figure 7:
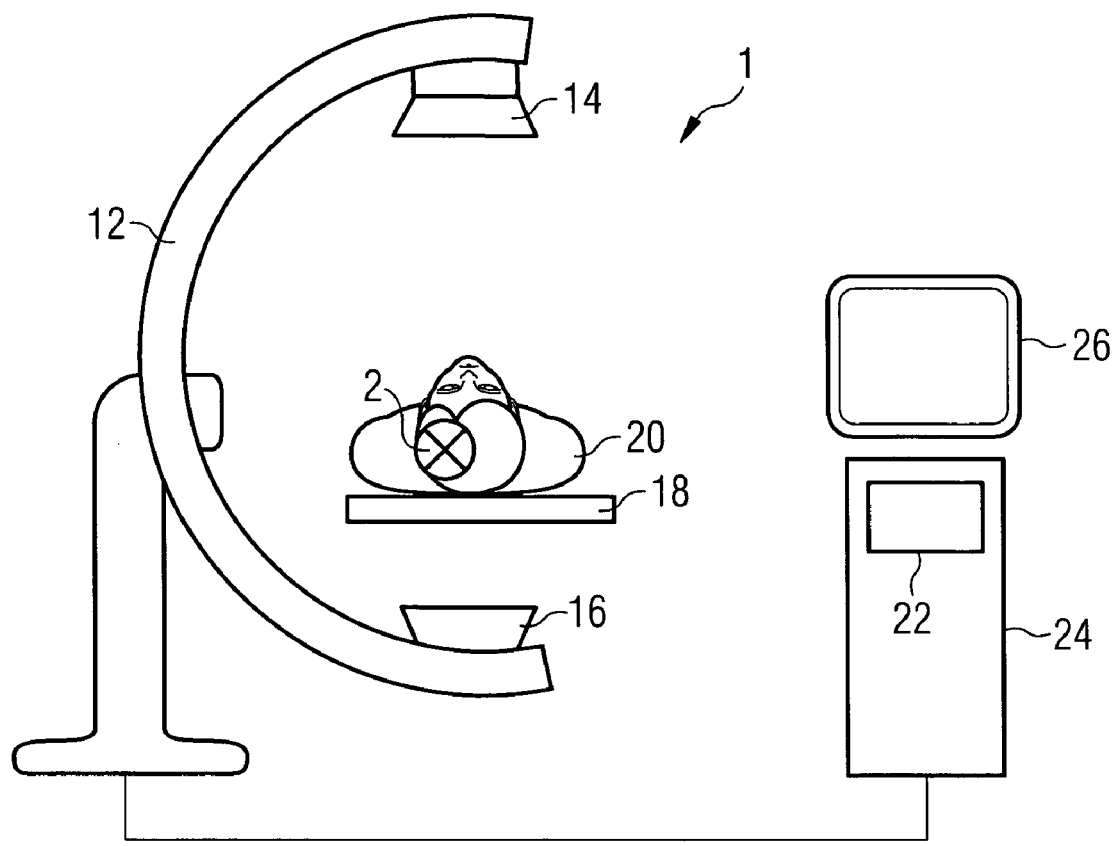
FIG. 7 shows a schematic diagram of an exemplary embodiment of a claimed device.

Finally FIG. 7 shows an x-ray imaging system 1, in which the claimed method can be implemented. It is a C-arm system with a C-arm 12, which can be moved freely about a patient support 18 and has an x-ray tube 14 and an x-ray detector 16 attached to it arms. A patient 20, whose heart 2 is to be examined, is lying on the support 18. As described above, the C-arm can thereby rotate about the patient in approx. 2 to 40 seconds, thereby recording numerous projection images from an angle range of over 180°. The image data is transmitted to an imaging processing computer 24, which contains a computing module 22. The projection images can be processed as described above in this computing module 22, resulting in a 3D image data set of the heart 2 with motion correction. This can be displayed on the screen 26.

A biplane device can also be used instead of the monoplane device 1 shown, thereby allowing two projection images to be recorded simultaneously in each instance.

The claimed method can also be used with multiple rotations of the C-arm. In this instance the motion field calculated using the local tomography is used to take into account the gaps that still remain in certain instances despite multiple rotations.

The claimed method is particularly suitable for the following applications: imaging of the coronary arteries after intravenous or intra-arterial injection of contrast agents; imaging of the chambers of the heart (atria, ventricles) after intravenous or intra-arterial injection of contrast agents, e.g. to plan interventional or electro-physiological procedures; imaging of the coronary veins to plan electro-physiological interventions.

The invention allows 3D reconstructions to be achieved with a high level of time resolution and few artifacts without time-consuming user interaction. Unlike most existing motion correction methods, this invention has the advantage that it can also be used for low-contrast objects, if edges can be mapped using local tomography. In particular the heart could be imaged thus using intravenous rather than intra-arterial injection.

The advantages compared with interactive methods are both the time saving and the wide applicability, in other words it can be used for any ECG-correlated moving structure and is not restricted to the heart or coronary arteries.

The method can also be used to correct other, periodic motion, e.g. respiratory motion. Ultimately almost all the organs of the thorax and abdomen are affected by respiratory motion, which is why tomographic recordings are currently made with the subject holding their breath. The respiratory phase can for example be determined using a spirometer and assigned to the projection images acquired at this time.

The method in this invention can also be combined with data acquisition by means of multiple rotations. This has the advantage that the time resolution can be further improved.

The invention claimed is:

1. A method for reconstructing a 3D image data set of a moving object from a set of projection images which are recorded at least partially one after the other from different projection directions, comprising:
    dividing the set of projection images into a plurality of subsets based on a specific motion phase of the moving object;
    reconstructing an incomplete 3D image of the moving object from each projection image of the subsets using a local tomography method, wherein the incomplete 3D image obtained using local tomography contains a segment of an intensity edge in the moving object and the segment is essentially parallel to a projection direction of a projection image belonging to an associated subset;
    determining a motion field of the moving object from the incomplete 3D image, the motion field showing a motion of the moving object between two successive motion phases;
    generating the 3D image data of the moving object with a motion correction effected by the motion field; and
    displaying a 3D image of the moving object based on the generated 3D image data.

2. The method as claimed in claim 1, wherein the incomplete 3D image is processed by supplementing the intensity edge by an interpolation between existing segments.

3. The method as claimed in claim 1, wherein the projection images are x-ray images which are recorded by an x-ray tube and an x-ray detector, the x-ray tube and the x-ray detector rotated about the moving object during recording.

4. The method as claimed in claim 1, wherein a motion status of the object is measured during recording and the projection images are assigned to an individual motion phase of the motion status of the moving object based on the measurement.

5. The method as claimed in claim 4, wherein, the moving object is a heart or an organ of a live human or animal body subject to a heartbeat and the motion status of the moving object is measured by an ECG.

6. The method as claimed in claim 5, wherein the projection images are assigned to a specific motion phase of the heart based on the ECG measurement.

7. A device for reconstructing a 3D image data set of a moving object from a set of projection images which are recorded at least partially one after the other from different projection directions, comprising:
 a dividing device for dividing the set of projection images into a plurality of subsets based on a specific motion phase of the moving object;
 a first computing module for reconstructing an incomplete 3D image of the moving object from each projection image of the subsets using a local tomography method, wherein the incomplete 3D image obtained using local tomography contains a segment of an intensity edge in the moving object and the segment is essentially parallel to a projection direction of a projection image belonging to an associated subset;
 a second computing module for determining a motion field of the moving object from the incomplete 3D image, the motion field showing a motion of the moving object between two successive motion phases; and
 a third computing module for generating the 3D image data of the moving object with a motion correction effected by the motion field.

8. The device as claimed in claim 7, wherein the device is an x-ray device having an x-ray tube and an x-ray detector which are movable about the moving object.

9. The device as claimed in claim 7, wherein the device is a C-arm system having an x-ray tube and an x-ray detector which are attached to a C-arm and rotate about the moving object.

10. The device as claimed in claim 7, wherein the moving object is a heart or an organ of a live human or animal body subject to a heartbeat and the motion statue of the moving object is measured by an ECG.

11. The device as claimed in claim 7, wherein the first, second, and third computing modules are stored in a single computer.

* * * * *